United States Patent [19]

Haas et al.

[11] 4,310,633

[45] Jan. 12, 1982

[54] HEXAHYDROTRIAZINE CARBOXYLATES AND THE USE THEREOF AS CATALYSTS IN THE PRODUCTION OF POLYISOCYANURATE PLASTICS

[75] Inventors: Peter Haas, Haan; Johannes Blahak, Cologne; Rolf Wiedermann, Bergisch-Gladbach, all of Fed. Rep. of Germany

[73] Assignee: Bayer Aktiengesellschaft, Leverkusen, Fed. Rep. of Germany

[21] Appl. No.: 206,112

[22] Filed: Nov. 12, 1980

Related U.S. Application Data

[62] Division of Ser. No. 51,789, Jun. 25, 1979, Pat. No. 4,260,754.

[30] Foreign Application Priority Data

Jul. 6, 1978 [DE] Fed. Rep. of Germany ....... 2829670

[51] Int. Cl.$^3$ ..................... C08G 18/14; C08G 18/20; C07D 251/04

[52] U.S. Cl. .................................. 521/129; 521/125; 521/128; 521/902; 521/121; 528/52; 528/53; 528/59; 544/215

[58] Field of Search ............... 521/902, 125, 128, 129; 528/52, 53, 57

[56] References Cited

U.S. PATENT DOCUMENTS

| | | | |
|---|---|---|---|
| 2,993,870 | 7/1961 | Burkus | 521/902 |
| 4,066,580 | 1/1978 | Falkenstein et al. | 521/129 |
| 4,148,980 | 4/1979 | Narayan | 521/128 |
| 4,256,841 | 3/1981 | Horacek et al. | 521/125 |

*Primary Examiner*—H. S. Cockeram
*Attorney, Agent, or Firm*—Gene Harsh; Joseph C. Gil; Lyndanne M. Whalen

[57] ABSTRACT

The instant invention is directed to hexahydrotriazine carboxylates, a method for their preparation, and their use as catalysts in the production of polyisocyanurate plastics.

5 Claims, No Drawings

HEXAHYDROTRIAZINE CARBOXYLATES AND THE USE THEREOF AS CATALYSTS IN THE PRODUCTION OF POLYISOCYANURATE PLASTICS

This application is a division of application Ser. No. 051,789, filed June 25, 1979, now U.S. Pat. No. 4,260,754.

BACKGROUND OF THE INVENTION

There are numerous known catalysts for the production of isocyanurate plastics. However, it has never been possible using the known catalysts to solve satisfactorily the problem of shrinkage which is mainly encountered in the case of polyisocyanurate foams having relatively long gel times.

It has surprisingly been found that polyisocyanurate foams which are resistant to shrinkage, even despite long gel times, may be obtained using the hexahydrotriazine carboxylates of the present invention.

The achievement of a high shrinkage stability may also be obtained by the combination of the catalysts of the present invention with other known polyurethane catalysts. Hitherto, in the production of polyisocyanurate foams, it has been possible to add only small quantities of polyurethane catalysts to the isocyanurate catalysts because otherwise shrinkage problems arise. The combination of polyurethane catalysts with the catalysts of the present invention enables the reaction to be controlled as required and any desired ratio to be adjusted between cream time and gel time without any shrinkage effects occurring.

DESCRIPTION OF THE INVENTION

The present invention relates to hexahydrotriazine carboxylates of the formula:

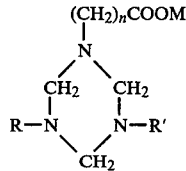 (I)

wherein
R and R', which may be the same or different, each represents

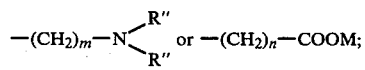

R" represents $C_1$–$C_3$ alkyl, preferably methyl;
m represents an integer of from 2 to 6, preferably from 2 to 4;
n represents an integer of from 1 to 10, preferably 1 to 4; and
M represents an alkali metal, preferably Na or K, or $NR'''_4$ ($R'''$ represents H or $C_1$–$C_4$ alkyl).

The present invention also relates to a process for the production of the above-mentioned hexahydrotriazine carboxylates comprising reacting equimolar quantities of formaldehyde and a compound of the formula:

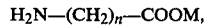

and optionally $H_2N$—R and/or $H_2N$—R' wherein
R and R', which may be the same or different, each represents

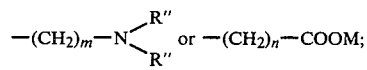

R" represents $C_1$–$C_3$ alkyl, preferably methyl;
m represents an integer of from 2 to 6, preferably from 2 to 4;
n represents an integer of from 1 to 10, preferably from 1 to 4; and
M represents an alkali metal, preferably Na or K, or $NR'''_4$ ($R'''$ represents H or $C_1$–$C_4$ alkyl).

The present invention also relates to the use of the above-mentioned hexahydrotriazines, optionally in combination with other known polyisocyanurate or polyurethane catalysts, as catalysts for the production of polyisocyanurate plastics.

According to the present invention, it is possible to use any compounds of the formula (I) above, for example the corresponding alkali metal salts, such as Li, Na, K, Rb or Cs salts, and ammonium salts, although it is preferred to use the Na and/or K salts.

The following are examples of hexahydrotriazine carboxylates according to the present invention:

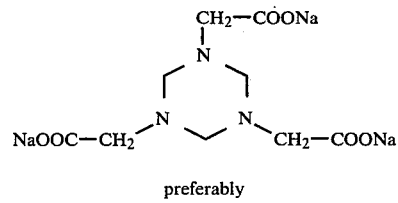

preferably

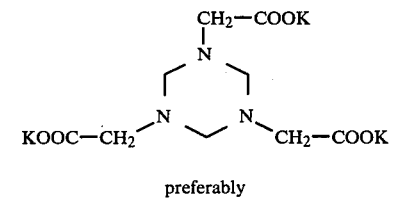

preferably

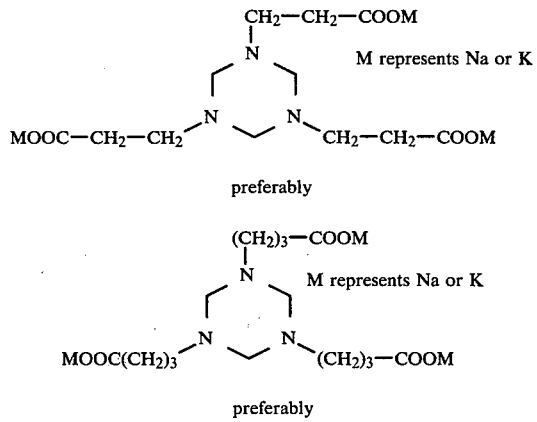

preferably

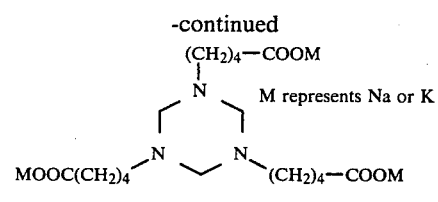
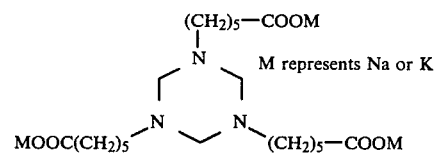
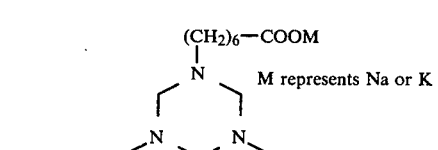
preferably
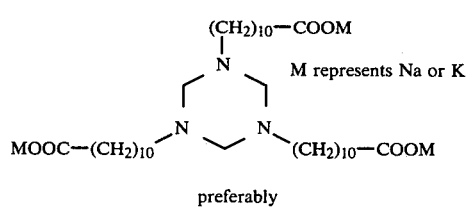
preferably
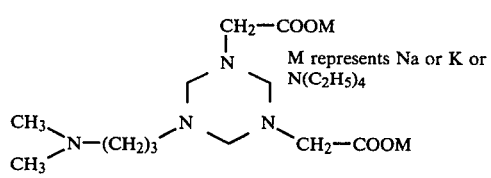
preferably
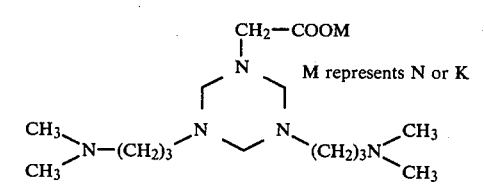
preferably
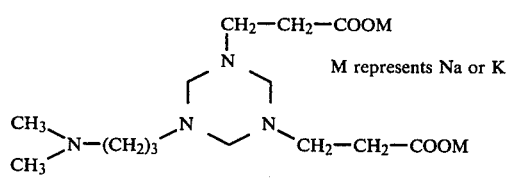
preferably
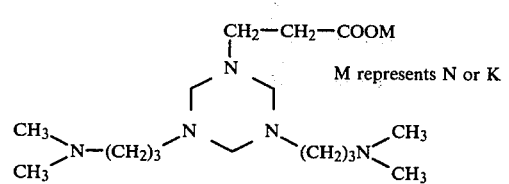
preferably
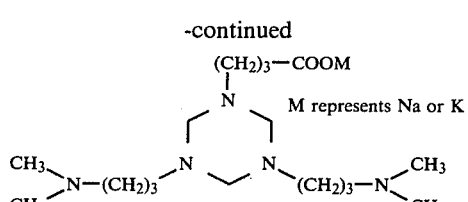
preferably
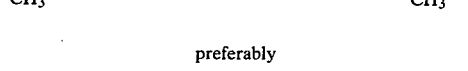
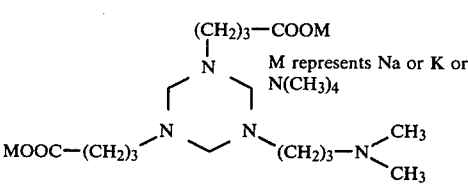
preferably
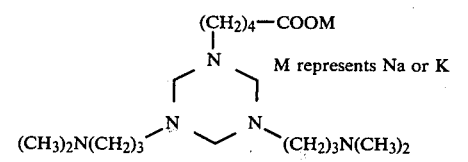
preferably
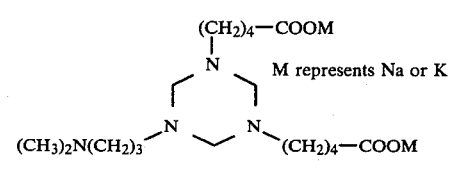
preferably
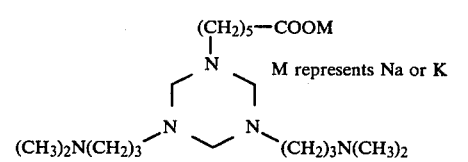
preferably
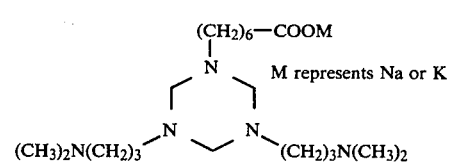
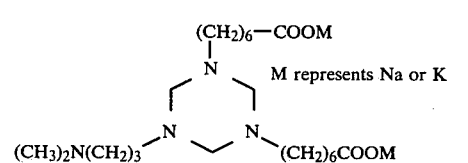
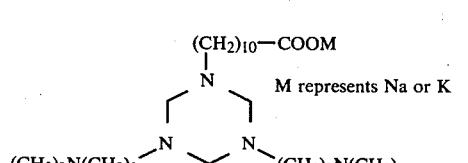

-continued

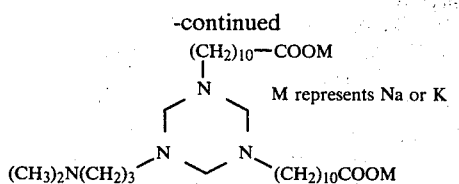

M represents Na or K

The compounds corresponding to above general formula (I) are obtained by analogous processes in which formaldehyde is condensed with the compound:

$$H_2N-(CH_2)_n-COOM,$$

and optionally $$H_2N-R \text{ and/or } H_2N-R'$$

wherein M, R, R' and n are as defined above. The reactants are generally used in equimolar quantities. The reaction may be carried out at room temperature or at elevated temperature, for example at 50° C. It is also possible to carry out condensation in the presence of inert solvents, such as water, ethanol or isopropanol. In general, formaldehyde is used in the form of an aqueous solution or in the form of paraformaldehyde or trioxane. Suitable compounds corresponding to the general formula:

$$H_2N-(CH_2)_n-COOM$$

include any compounds which fall within the scope of this definition, although it is preferred to use the salts of glycine, $\beta$-aminopropionic acid, $\gamma$-aminobutyric acid, $\epsilon$-aminocaproic acid and 11-aminoundecanoic acid. Suitable compounds corresponding to the general formulae:

$$H_2N-R \text{ and } H_2N-R'$$

are again any compounds which fall within the scope of this definition, $\gamma$-dimethylaminopropyl amine, $\beta$-dimethylaminoethyl amine and $\delta$-dimethylaminobutyl amine, for example, being particularly suitable.

Condensation to form the hexahydrotriazine is carried out, for example, with the azeotopic removal of water from the reaction mixture, preferably using toluene.

The compounds corresponding to above general formula (I) according to the present invention are generally used as catalysts in the production of polyisocyanurate plastics in a quantity of from 0.01 to 20%, by weight, preferably from 0.1 to 10%, by weight, based on the polyisocyanates present. The catalyst is preferably in the form of a solution in alcohols, such as ethylene glycol, diethylene glycol, dipropylene glycol and tripropylene glycol.

The production of polyisocyanurate plastics is known. The starting components used for this purpose are:

(1) aliphatic, cycloaliphatic, araliphatic, aromatic and heterocyclic polyisocyanates of the type described, for example, by W. Siefken in Justus Liebigs Annalen der Chemie, 562, pages 75 to 136, for example those of the formula:

$$Q(NCO)_n$$

wherein
n represents from 2 to 4, preferably 2; and
Q represents an aliphatic hydrocarbon radical containing from 2 to 18 carbon atoms, preferably from 6 to 10 carbon atoms;
a cycloaliphatic hydrocarbon radical containing from 4 to 15 carbon atoms, preferably from 5 to 10 carbon atoms;
an aromatic hydrocarbon radical containing from 6 to 15 carbon atoms, preferably from 6 to 13 carbon atoms;
or an araliphatic hydrocarbon radical containing from 8 to 15 carbon atoms, preferably from 8 to 13 carbon atoms.

Examples of possible isocyanates include ethylene diisocyanate, 1,4-tetramethylene diisocyanate, 1,6-hexamethylene diisocyanate, 1,12-dodecane diisocyanate, cyclobutane-1,3-diisocyanate, cyclohexane-1,3- and 1,4-diisocyanate and mixtures of these isomers, 1-isocyanato-3,3,5-trimethyl-5-isocyanatomethyl cyclohexane (German Auslegeschrift No. 1,202,785, U.S. Pat. No. 3,401,190), 2,4- and 2,6-hexahydrotolylene diisocyanate and mixtures of these isomers, hexahydro-1,3- and/or -1,4-phenylene diisocyanate, perhydro-2,4'- and/or -4,4'-diphenyl methane diisocyanate, 1,3- and 1,4-phenylene diisocyanate, 2,4- and 2,6-tolylene diisocyanate and mixtures of these isomers, diphenyl methane-2,4'- and/or -4,4'-diisocyanate and naphthylene-1,5-diisocyanate.

It is also possible to use triphenyl methane-4,4',4"-triisocyanate; polyphenyl polymethylene polyisocyanates (British Pat. Nos. 874,430 and 848,671), m- and p-isocyanatophenyl sulfonyl isocyanates (U.S. Pat. No. 3,454,606), perchlorinated aryl polyisocyanates (German Auslegeschrift No. 1,157,601 and U.S. Pat. No. 3,277,138), polyisocyanates containing carbodiimide groups (German Pat. No. 1,092,007, U.S. Pat. No. 3,152,162 and German Offenlegungsschriften Nos. 2,504,400; 2,537,685 and 2,552,530), norbornane diisocyanates (U.S. Pat. No. 3,492,330), polyisocyanates containing allophanate groups (British Pat. No. 994,890, Belgian Pat. No. 761,626 and Dutch Patent Application No. 7,102,524), polyisocyanates containing isocyanurate groups (U.S. Pat. No. 3,001,973; German Pat. Nos. 1,022,789; 1,222,067 and 1,027,394 and German Offenlegungsschriften Nos. 1,929,034 and 2,004,048), polyisocyanates containing urethane groups (Belgian Pat. No. 752,261 and U.S. Pat. Nos. 3,394,164 and 3,644,457), polyisocyanates containing acylated urea groups (German Pat. No. 1,230,778), polyisocyanates containing biuret groups (U.S. Pat. Nos. 3,124,605; 3,201,372 and 3,124,605 and British Pat. No. 889,050), polyisocyanates produced by telomerization reactions (U.S. Pat. No. 3,654,106), polyisocyanates containing ester groups (British Pat. Nos. 965,474 and 1,072,956, U.S. Pat. No. 3,567,763 and German Pat. No. 1,231,688), reaction products of the above-mentioned diisocyanates with acetals (German Pat. No. 1,072,385) and polyisocyanates containing polymeric fatty acid esters (U.S. Pat. No. 3,455,883).

It is also possible to use the isocyanate group-containing distillation residues obtained in the commercial production of isocyanates, optionally in solution in one or more of the above-mentioned polyisocyanates. It is also possible to use mixtures of the above-mentioned polyisocyanates.

In general, it is particularly preferred to use readily available polyisocyanates, for example 2,4- and 2,6-tolylene diisocyanate, and mixtures of these isomers ("TDI"); polyphenyl polymethylene polyisocyanates of the type obtained by condensing aniline with formaldehyde, followed by phosgenation ("crude MDI"); and polyisocyanates containing carbodiimide groups, urethane groups, allophanate groups, isocyanurate groups, urea groups or biuret groups ("modified polyisocyanates"), and particularly modified polyisocyanates of the type derived from 2,4- and/or 2,6-tolylene diisocyanate or from 4,4'- and/or 2,4'-diphenyl methane diisocyanate.

(2) Additional starting components for the production of polyisocyanurate plastics can include compounds containing at least two isocyanate-reactive hydrogen atoms preferably having a number average molecular weight as determined by gel permeation chromatography of from 400 to 10,000. The active hydrogen component should be used in such quantities that at least 25%, by weight, of the isocyanate groups originally present in the polyisocyanates remain free for the trimerization reaction. Compounds containing amino groups, thiol groups, carboxyl groups or hydroxyl groups may be used. The preferred compounds are those containing hydroxyl groups, particularly compounds containing from 2 to 8 hydroxyl groups and, above all, compounds having molecular weights of from 800 to 5000, and preferably from 800 to 3000. The preferred compounds are polyesters, polyethers, polythioethers, polyacetals, polycarbonates and polyester amides containing at least two, generally from 2 to 8, but preferably from 2 to 4 hydroxyl groups, of the type generally known for the production of non-cellular and cellular polyurethanes;

(a) The polyesters containing hydroxyl groups suitable for use in the present invention are reaction products of polyhydric (preferably dihydric and, optionally, trihydric), alcohols with polybasic, (preferably dibasic), carboxylic acids. Instead of using the free polycarboxylic acids, it is also possible to use the corresponding polycarboxylic acid anhydrides or corresponding polycarboxylic acid esters of lower alcohols or mixtures thereof for producing the polyesters. The polycarboxylic acids may be aliphatic, cycloaliphatic, aromatic and/or heterocyclic and may optionally be substituted, for example by halogen atoms and/or they may be unsaturated.

Examples of such carboxylic acids and derivatives thereof include: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylene tetrahyrophthalic acid anhydride, glutaric acid anhydride, maleic acid, maleic acid anhydride, fumaric acid, dimerized and trimerized unsaturated fatty acids, optionally in admixture with monomeric unsaturated fatty acids, such as oleic acid; terephthalic acid dimethyl ester and terephthalic acid-bis-glycol ester. Suitable polyhydric alcohols are, for example, ethylene glycol, 1,2- and 1,3-propylene glycol, 1,4- and 2,3-butylene glycol, 1,6-hexane diol, 1,8-octane diol, neopentyl glycol, 1,4-bis-hydroxymethyl cyclohexane, 2-methyl-1,3-propane diol, glycerol, trimethylol propane, 1,2,6-hexane triol, 1,2,4-butane triol, trimethylol ethane, pentaerythritol, quinitol, mannitol, sorbitol, formitol, methyl glycoside, diethylene glycol, triethylene glycol, tetraethylene glycol and higher polyethylene glycols, dipropylene glycol and higher polypropylene glycols, dibutyl glycol and higher polybutylene glycols. The polyesters may contain terminal carboxyl groups. Polyesters of lactones, for example ε-caprolactone, or of hydroxy carboxylic acids, for example ω-hydroxy caproic acid, may also be used.

(b) The polyesters containing at least two, generally from 2 to 8, preferably 2 or 3, hydroxyl groups suitable for use in the present invention are also known. They may be obtained by polymerizing epoxides such as ethylene oxide, propylene oxide, butylene oxide, tetrahydrofuran, styrene oxide or epichlorhydrin, or their own, for example in the presence of Lewis catalysts, such as BF$_3$, or by the addition of these epoxides optionally in admixture or successively, with starter components containing reactive hydrogen atoms. Reactive hydrogen containing compounds include water, ammonia, alcohols or amines. Examples include ethylene glycol, 1,3- or 1,2-propylene glycol, trimethylol propane, glycerol, sorbitol 4,4'-dihydroxy diphenyl propane, aniline, ethanolamine or ethylene diamine. Sucrose polyethers (German Auslegeschriften Nos. 1,176,358 and 1,064,938) and formitol- or formose-started polyethers (German Offenlegungsschriften Nos. 2,639,083 and 2,737,951) may also be used in the present invention. In many cases, it is preferred to use polyethers which contain predominant amounts of primary OH-groups (up to 90%, by weight, based on all the OH-groups present in the polyether). Polybutadienes containing OH-groups are also suitable for use in the present invention.

(c) Among the polythioethers, particular reference is made to the condensation products of thiodiglycol on its own and/or with other glycols, dicarboxylic acids, formaldehyde, aminocarboxylic acids or amino alcohols. Depending on the co-components, the products in question are polythio mixed ethers, polythioether esters or polythioether ester amides.

(d) Suitable polyacetals include, for example, the compounds obtainable by reaction of glycols, such as diethylene glycol, triethylene glycol, 4,4'-dioxethoxy diphenyl dimethyl methane and hexane diol, with formaldehyde. Polyacetals suitable for use in the present invention may also be obtained by polymerizing cyclic acetals, such as trioxane (German Offenlegungsschrift No. 1,694,128).

(e) Suitable polycarbonates containing hydroxyl groups are known and may be obtained by reacting diols with diaryl carbonates, for example diphenyl carbonate, or with phosgene (German Auslegeschriften Nos. 1,694,080; 1,915,908 and 2,221,751; German Offenlegungsschrift No. 2,605,024). Diols which may be used include 1,3-propane diol, 1,4-butane diol and/or 1,6-hexane diol, diethylene glycol, triethylene glycol, tetraethylene glycol or thiodiglycol.

(f) The polyester amides and polyamides include, for example, the predominantly linear condensates obtained from polybasic saturated or unsaturated carboxylic acids or anhydrides thereof and polyfunctional saturated or unsaturated amino alcohols, diamines, polyamines and mixtures thereof.

(g) Polyhydroxyl compounds already containing urethane or urea groups and optionally modified natural polyols, such as castor oil, or carbohydrates, for example starch, may also be used. Addition products of alkylene oxides with phenol/formaldehyde resins or even with urea/formaldehyde resins may also be used in the present invention.

(h) Before they are used in the polyisocyanate-polyaddition process, the above-mentioned polyhyroxyl compounds may be modified in various ways. In German Offenlegungsschriften Nos. 2,210,839 (U.S. Pat. No. 3,849,515) and 2,544,195, a mixture of different polyhyroxyl compounds (for example a polyether polyol and a polyester polyol) may be condensed by etherification in the presence of a strong acid to form a relatively high molecular weight polyol which is made up of different segments attached by ether bridges. It is also possible to introduce amide groups into the polyhydroxyl compounds (German Offenlegungsschrift No. 2,559,372) or to introduce triazine groups by reaction with polyfunctional cyanic acid esters (German Offenlegungsschrift No. 2,620,487). The reaction of a polyol with a sub-equivalent quantity of a diisocyanatocarbodiimide, followed by reaction of the carbodiimide group with an amine, amide, phosphite or carboxylic acid, gives polyhydroxyl compounds containing guanidine, phosphono-formamidine or acyl urea groups (German Offenlegungsscriften Nos. 2,714,289; 2,714,292 and 2,714,293). In some cases, it is particularly advantageous to completely or partly convert the relatively high molecular weight polyhydroxyl compounds into the corresponding anthranilic acid esters by reaction with isatoic acid anhydride (German Offenlegungschriften Nos. 2,019,432 and 2,619,840 and U.S. Pat. Nos. 3,808,250; 3,975,428 and 4,016,143). Relatively high molecular weight compounds containing terminal aromatic amino groups are obtained in this way.

According to German Offenlegungsschrift No. 2,546,536 and U.S. Pat. No. 3,865,791, relatively high molecular weight compounds containing terminal amino groups are obtained by reacting NCO prepolymers with enamines, aldimines or ketimines containing hydroxyl groups, followed by hydrolysis. Additional processes for producing relatively high molecular weight compounds containing terminal amino groups or hydrazide groups are described in German Offenlegungsschrift No. 1,694,152 (U.S. Pat. No. 3,625,871).

(i) It is also possible to use polyhydroxyl compounds containing high molecular weight polyadducts and polycondensates or polymers in finely disperse or dissolved form. Such polyhydroxyl compounds are obtained by carrying out polyaddition reactions (for example reactions between polyisocyanates and aminofunctional compounds) and polycondensation reactions (for example between formaldehyde and phenols and/or amines) in situ in the above-mentioned compounds containing a hydroxyl groups. Such processes are described in German Auslegeschriften Nos. 1,168,075 and 1,260,142 and German Offenlegungsschriften Nos. 2,324,134; 2,423,984; 2,512,385; 2,513,815; 2,550,796; 2,550,797; 2,550,833; 2,550,862; 2,633,293 and 2,639,254. It is also possible to mix an aqueous polymer dispersion with a polyhydroxyl compound and subsequently to remove the water from the mixture (U.S. Pat. No. 3,869,413 or German Offenlegungsschrift No. 2,550,860).

Polyhydroxyl compounds modified by vinyl polymers of the type obtained by polymerizing styrene and acrylonitrile in the presence of polyethers (U.S. Pat. Nos. 3,383,351; 3,304,273; 3,523,093 and 3,110,695; German Auslegeschrift No. 1,152,536), or polycarbonate polyols (German Pat. No. 1,769,795 or U.S. Pat. No. 3,637,909) are also suitable for use in the process of the present invention. Plastics having particularly good flameproof properties are obtained by using polyether polyols modified as described in German Offenlegungsschriften Nos. 2,442,101; 2,644,922 and 2,646,141 by graft polymerization with vinyl phosphonic acid esters and, optionally, (meth)acrylonitrile, (meth)acrylamide or OH-functional (meth)acrylic acid esters. Polyhydroxyl compounds into which carboxyl groups have been introduced by radical graft polymerization with unsaturated carboxylic acids and, optionally, other olefinically unsaturated monomers (German Offenlegungsschrift Nos. 2,714,291; 2,739,620 and 2,654,746) may be used with particular advantage in combination with mineral fillers.

Where modified polyhydroxyl compounds of the type mentioned above are used as starting component in the polyisocyanate-polyaddition process, polyurethanes having considerably improved mechanical properties are formed in many cases.

Representatives of the above-mentioned compounds in accordance with the present invention are known and are described, for example, in High Polymers, Vol. XVI, "Polyurethanes, Chemistry and Technology", by Saunders-Frisch, Interscience Publishers, New York/London, Vol. I, 1962, pages 32 to 42 and pages 44 to 54 and Vol. II, 1964, pages 5–6 and 198–199, and in Kunststoff-Handbuch, Vol. VII, Vieweg-Hochtlen, Carl-Hanser-Verlag, Munich, 1964, for example on pages 45 to 71. It is, of course, possible to use mixtures of the above-mentioned compounds containing at least two isocyanate-reactive hydrogen atoms and having a molecular weight of from 400 to 10,000, for example mixtures of polyethers and polyesters.

In some cases, it is particularly advantageous to combine low melting and high melting polyhydroxyl compounds with one another (German Offenlegungsschrift No. 2,706,297).

(3) The reaction mixture may also include compounds containing at least two isocyanate-reactive hydrogen atoms having a number average molecular weight of from 32 to 400 as determined by gel permeation chromatography. In this case, too, the compounds in question are compounds containing hydroxyl groups and/or amino groups and/or thiol groups and/or carboxyl groups, preferably compounds containing hydroxyl groups and/or amino groups which serve as chain-extenders or cross-linkers. These compounds generally contain from 2 to 8, preferably from 2 to 4, isocyanate-reactive hydrogen atoms. In this case, too, it is possible to use mixtures of different compounds containing at least two isocyanate-reactive hydrogen atoms and having a molecular weight of from 32 to 400.

Examples of such compounds include ethylene glycol, 1,2- and 1,3-propylene glycol, 1,4- and 2,3-butylene glycol, 1,5-pentane diol, 1,6-hexane diol, 1,8-octane diol, neopentyl glycol, 1,4-bis-hydroxymethyl cyclohexane, 2-methyl-1,3-propane diol, dibromobutene diol (U.S. Pat. No. 3,723,392), glycerol, trimethylol propane, 1,2,6-hexane triol, trimethylol ethane, pentaerythritol, quinitol, mannitol, sorbitol, castor oil, diethylene glycol, triethylene glycol, tetraethylene glycol, higher polyethylene glycols having a molecular weight of up to 400, dipropylene glycol, higher polypropylene glycols having a molecular weight of up to 400, dibutyl glycol, higher polybutylene glycols having a molecular weight of up to 400, dibutylene glycol, higher polybutylene glycols having a molecular weight of up to 400, 4,4'-dihydroxy diphenyl propane, dihydroxy methyl hydroquinone, ethanolamine, diethanolamine, N-methyl diethanolamine, triethanolamine and 3-aminopropanol.

Other low molecular weight polyols suitable for the purposes of the present invention are the mixtures of hyroxy aldehydes and hydroxy ketones ("formose") or the polyhydric alcohols obtained therefrom by reduction ("formitol") which are formed in the autocondensation of formaldehyde hydrate in the presence of metal compounds as catalysts and compounds capable of enediol formation as co-catalysts (German Offenlegungsschriften Nos. 2,639,084; 2,714,084; 2,714,104; 2,721,186; 2,738,154 and 2,738,512). Solutions of polyisocyanate polyaddition products, particularly solutions of polyurethane ureas containing ionic groups and/or solutions of polyhydrazodicarbonamides, in low molecular weight polyhydric alcohols may also be used as the polyol component in the present invention (German Offenlegungsschrift No. 2,638,759).

Solutions of polyisocyanate polyaddition products, particularly solutions of polyurethane ureas containing ionic groups and/or solutions of polyhydrazodicarbonamides, in low molecular weight polyhydric alcohols may also be used as the polyol component in the present invention (German Offenlegungsschrift No. 2,638,759).

Aliphatic diamines suitable for use in the present invention include ethylene diamine, 1,4-tetramethylene diamine, 1,11-undecamethylene diamine, 1,12-dodecamethylene diamine and mixtures thereof, 1-amino-3,3,5-trimethyl-5-aminomethyl cyclohexane ("isophorone diamine"), 2,4- and 2,6-hexahydrotolylene diamine and mixtures thereof, perhydro-2,4'- and -4,4'-diaminodiphenyl methane, p-xylylene diamine, bis-(3-aminopropyl)-methylamine, diaminoperhydro anthracenes (German Offenlegungsschrift No. 2,638,731) and cycloaliphatic triamines (German Offenlegungsschrift No. 2,614,244). It is also possible in the present invention to use hydrazine and substituted hydrazines, for example methyl hydrazine, N,N'-dimethyl hydrazine and homologues thereof and also acid dihydrazides, for example carbodihydrazide, oxalic acid dihydrazide, the dihydrazides of malonic acid, succinic acid, glutaric acid, adipic acid, β-methyl adipic acid, sebacic acid, hydracrylic acid and terephthalic acid; semicarbazido alkylene hydrazides, such as β-semicarbazido propionic acid hydrazide (German Offenlegungsschrift No. 1,770,591), semicarbazido alkylene carbazinic esters, such as 2-semicarbazido ethyl carbazinic ester (German Offenlegungsschrift No. 1,918,504) or even aminosemicarbazide compounds, such as β-aminoethyl semicarbazido carbonate (German Offenlegungsschrift No. 1,902,931). To control the reactivity thereof, the amino groups may be completely or partly blocked by aldimine or ketimine groups (U.S. Pat. No. 3,734,894 or German Offenlegungsschrift No. 2,637,115).

Examples of aromatic diamines include: bisanthranilic acid esters (German Offenlegungsschriften Nos. 2,040,644 and 2,160,590), 3,5- and 2,4-diaminobenzoic acid esters (German Offenlegungsschrift No. 2,025,900), the diamines containing ester groups (German Offenlegungsschriften Nos. 1,803,635; 2,040,650 and 2,160,589, and U.S. Pat. Nos. 3,681,290 and 3,736,350), the diamines containing ether groups (German Offenlegungsschriften Nos. 1,770,525 and 1,809,172 and U.S. Pat. Nos. 3,654,364 and 3,736,295), 2-halogen-1,3-phenylene diamines optionally substituted in the 5-position (German Offenlegungsschriften Nos. 2,011,722; 2,025,896 and 2,065,869) 3,3'-dichloro-4,4'-diaminodiphenyl methane, tolylene diamine, 4,4'-diaminodiphenyl methane, 4,4'-diaminodiphenyl disulfides (German Offenlegungsschrift No. 2,404,976), diaminodiphenyl dithio ethers (German Offenlegungsschrift No. 2,509,404), aromatic diamines substituted by alkyl thio groups (German Offenlegungsschrift No. 2,638,760), diaminobenzene phosphonic acid esters (German Offenlegungsschrift No. 2,459,491), aromatic diamines containing sulfonate or carboxylate groups (German Offenlegungsschrift No. 2,720,166) and the high-melting diamines described in German Offenlegungsschrift No. 2,635,400. Examples of aliphatic-aromatic diamines include amino-alkyl thioanilines (German Offenlegungsschrift No. 2,734,574).

Other suitable chain-extenders include: 1-mercapto-3-aminopropane, optionally substituted amino acids, for example glycine, alanine, valine, serine and lysine; and optionally substituted dicarboxylic acids, for example succinic acid, adipic acid, phthalic acid, 4-hydroxy phthalic acid and 4-aminophthalic acid.

In addition, isocyanate-monofunctional compounds may be used as so-called "chain-terminators" in proportions of from 0.01 to 10%, by weight, based on polyurethane solids. Such monofunctional compounds include monoamines, such as butyl- and dibutyl-amine, octylamine, stearylamine, N-methyl stearylamine, pyrrolidine, piperidine and cyclohexylamine; and monohydricalcohols, such as butanol, 2-ethyl hexanol, octanol, dodecanol, the various amyl alcohols, cyclohexanol, and ethylene glycol monoethyl ether.

(4) It is also possible to include as optional additives and auxiliaries:

(a) Water and/or readily volatile inorganic or organic substances as blowing agents. Organic blowing agents include, acetone, ethyl acetate; halogen-substituted alkanes, such as methylene chloride, chloroform, ethylidene chloride, vinyldene chloride, monofluorotrichloromethane, chlorodifluoromethane, dichlorodifluoromethane; butane; hexane; heptane and diethyl ether. Inorganic blowing agents include air, $CO_2$ or $N_2O$. A blowing effect may also be obtained by adding compounds which decompose at temperatures above room temperature giving off gases for example azo compounds, such as azodicarbonamide or azoisobutyronitrile. Other examples of blowing agents and information on the use of blowing agents may be found in Kunststoff-Handbuch, Vol. VII, by Vieweg and Hochtlen, Carl-Hanser-Verlag, Munich, 1966, for example on pages 108 and 109, 453 to 455 and 507 to 510.

(b) Also known catalysts, for example tertiary amines, such as triethylamine, tributylamine, N-methyl morpholine, N-ethyl morpholine, N,N,N',N'-tetramethyl ethylene diamine, pentamethyl diethylene triamine and higher homologues (German Offenlegungsschriften Nos. 2,624,527 and 2,624,528), 1,4-diazabicyclo-(2,2,2)-octane, N-methyl-N'-dimethylaminoethyl piperidine, bis-(dimethylaminoalkyl)-piperazines (German Offenlegungsschrift No. 2,636,787), N,N-dimethyl benzylamine, N,N-dimethyl cyclohexylamine, N,N-diethyl benzylamine, bis-(N,N-diethylaminoethyl)-adipate, N,N,N',N'-tetramethyl-1,3-butane diamine, N,N-dimethyl-β-phenyl ethylamine, 1,2-dimethyl imidazole, 2-methyl imidazole, monocyclic and bicyclic amidines (German Offenlegungsschrift No. 1,720,633), bis-(dialkylamino)-alkyl ethers (U.S. Pat. No. 3,330,782, German Auslegeschrift No. 1,030,558, German Offenlegungsschriften Nos. 1,804,361 and 2,618,280) and tertiary amines containing amide groups, preferably formamide groups, (German Offenlegungsschriften Nos. 2,523,633 and 2,732,292).

Suitable catalysts also include known Mannich bases of secondary amines, such as dimethylamine; and aldehydes, preferably formaldehyde; or ketones, such as acetone, methylethyl ketone or cyclohexanone; and phenols, such as phenol, nonyl phenol or bisphenol.

Tertiary amines containing isocyanate-reactive hydrogen atoms suitable for use as catalysts include triethanolamine, triisopropanolamine; N-methyl diethanolamine; N-ethyl diethanolamine; N,N-dimethyl ethanolamine; the reaction products thereof with alkylene oxides, such as propylene oxide and/or ethylene oxide; and secondary-tertiary amines (German Offenlegungsschrift No. 2,732,292).

Other suitable catalysts are sila-amines containing carbon-silicon bonds (German Pat. No. 1,229,290 or U.S. Pat. No. 3,620,984), for example 2,2,4-trimethyl-2-silamorpholine and 1,3-diethylaminomethyl tetramethyl disiloxane.

Other suitable catalysts are nitrogen-containing bases, such as tetraalkyl ammonium hydroxides; alkali metal hydroxides, such as sodium hydroxide; alkali metal phenolates, such as sodium phenolate; or alkali metal alcoholates, such as sodium methylate. Hexahydrotriazines may also be used as catalysts (German Offenlegungsschrift No. 1,769,043).

The reaction between NCO-groups and Zerewitinoff-active hydrogen atoms is also greatly accelerated by lactams and azalactams, an associate between the lactam and the compound containing acid hydrogen initially being formed. Such associates and the catalytic effect thereof are described in German Offenlegungsschriften Nos. 2,062,288; 2,062,289; 2,117,576 (U.S. Pat. No. 3,758,444); 2,129,198; 2,330,175 and 2,330,211.

It is also possible to use organo-metallic compounds, particularly organo-tin compounds, as catalysts. In addition to sulfur-containing compounds, such as di-n-octyl tin mercaptide (German Auslegeschrift No. 1,769,367 or U.S. Pat. No. 3,654,927), preferred organo-tin compounds are tin(II)salts of carboxylic acids, such as tin(II)acetate, tin(II)octoate, tin(II)ethyl hexoate and tin(II)laurate. Also preferred are tin(IV)compounds, for example dibutyl tin oxide, dibutyl tin dichloride, dibutyl tin diacetate, dibutyl tin dilaurate, dibutyl tin maleate or dioctyl tin diacetate.

The above-mentioned catalysts may be used in the form of mixtures. In this respect, mixtures of organometallic compounds and amidines, aminopyridines or hydrazino pyridines (German Offenlegungsschriften Nos. 2,434,185; 2,601,082 and 2,603,834) are of particular interest.

Further representatives of catalysts suitable for use in the present invention and information on the way in which they work may be found in Kunststoff-Handbuch by Vieweg and Hochtlen, Vol. VII, Carl-Hanser-Verlag, Munich 1966, for example on pages 96 to 102.

These catalysts which may also be used in the present invention are generally used in a quantity of up to 50%, by weight, based on the total quantity of compunds corresponding to above general formula (I) used.

(c) Surface-active additives, such as emulsifiers and foam stabilizers. Suitable emulsifiers are the sodium salts of castor ol sulfonates or salts of fatty acids with amines, such as diethylamine oleate or diethanolamine stearate. Alkali metal or ammonium salts of sulfonic acids, such as dodecyl benzene sulfonic acid or dinaphthyl methane disulfonic acid; or of fatty acids, such as ricinoleic acid; or of polymeric fatty acids may also be used as surface-active additives. Suitable foam stabilizers include polyether siloxanes, particularly water-soluble types. The structure of these compounds is generally such that a copolymer of ethylene oxide and propylene oxide is attached to a polydimethyl siloxane residue. Such foam stabilizers are described in U.S. Pat. Nos. 2,834,748; 2,917,480 and 3,629,308. In many cases, polysiloxane-polyoxyalkylene copolymers branched through allophanate groups (German Offenlegungsschrift No. 2,558,523) are of particular interest.

(d) The following may also be included, reaction retarders, stabilizers against the effects of ageing and weather, plasticizers and fungistatic and bacteriostatic substances, as well as fillers. Reaction retarders include acid-reacting substances, such as hydrochloric acid or organic acid halides. Cell regulators include paraffins or fatty alcohols or dimethyl polysiloxanes. Flameproofing agents include for example tris-chloroethyl phosphate, tricresyl phosphate or ammonium phosphate and polyphosphate. Fillers include barium sulphate, keiselguhr, carbon black or whiting.

Further examples of surface-active additives and foam stabilizers, cell regulators, reaction retarders, stabilizers, flameproofing agents, plasticizers, dyes, fillers, fungistatic and bacteriostatic substances which may optionally be used in the present invention and information on the way in which these additives are used and on their respective modes of action may be found in Kunststoff-Handbuch by Vieweg and Hochtlen, Vol. VII, Carl-Hanser-Verlag, Munich 1966, for example on pages 103 to 113.

The process of the present invention is carried out as follows:

The reaction components are reacted by the known one-shot process, by the prepolymer process or by the semi-prepolymer process, in many cases using machines of the type described in U.S. Pat. No. 2,764,565. Particulars of processing machines which may also be used in accordance with the present invention may be found in Kunststoff-Handbuch by Vieweg and Hochten, Vol. VII, Carl-Hanser-Verlag, Munich, 1966, on pages 121 to 205.

In the production of foams, it is also possible in accordance with the present invention to carry out foaming in closed molds. Suitable mold materials are metals or plastics, for example aluminum or epoxide resin. The foamable reaction mixture foams in the mold and forms the molding. In-mold foaming may be carried out in such a way that the molding has a cellular structure at its surface, although it may also be carried out in such a way that the molding has a compact skin and a cellular core. It is possible to introduce foamable reaction mixture into the mold in such a quantity that the foam formed completely fills the mold. However, it is also possible to introduce into the mold more foamable reaction mixture than is required for filling the interior of the mold with foam. This particular technique is known as "overcharging" (U.S. Pat. Nos. 3,178,490 and 3,182,104).

In many cases, known "external release agents" such as silicone oils, are used for in-mold foaming. However, it is also possible to use so-called "internal release agents", optionally in admixture with external release agents (German Offenlegungsschriften Nos. 2,121,670 and 2,307,589).

According to the present invention, it is also possible to produce cold-hardening foams (British Pat. No. 1,162,517 and German Offenlegungsschrift No. 2,153,086).

However, it is, of course, also possible to produce foams by block foaming or by the known laminator process.

The products obtainable in accordance with the present invention may be used for example, as insulating panels in the construction industry, for insulating pipes (half shells) and for floor insulation in cold-storage depots.

EXAMPLE 1

Tris-sodium acetyl hexahydrotriazine 40 g of NaOH and 75 g of glycine are dissolved in 100 ml of water, 30 g of paraformaldehyde are added and dissolved, after which the water is removed with toluene, followed by filtration under suction and drying. The aminal structure is confirmed by $^1$H NMR.

Analysis for $Na_3C_9H_{12}N_3O_6$: Calculated: C, 33.4% H, 3.7% N, 13.0%; Observed: C, 32.0% H, 4.5% N, 12.5%.

EXAMPLE 2

Tris-potassium acetyl hexahydrotriazine 56 g of KOH and 75 g of glycine are dissolved in 100 ml of water, 30 g of paraformaldehyde are added and dissolved and the water is removed with toluene, followed by filtration under suction and drying. The aminal structure was confirmed $^1$H NMR.

Analysis for $K_3C_9H_{12}N_3O_6$: Calculated: C, 29.1% H, 3.2% N, 11.2%; Observed: C, 30.0% H, 4.2% N, 10.5%.

EXAMPLE 3

Bis-sodium acetyl-γ-dimethylaminopropyl hexahydrotriazine 40 g of NaOH, 75 g of glycine, 51 g of γ-dimethylaminopropyl amine and 45 g of paraformaldehyde are added to 100 ml of water. The water is then removed with toluene, followed by filtration under suction and drying.

Analysis for $Na_2C_{12}H_{22}N_4O_4$: Calculated: C, 39.6% H, 6.05% N, 15.3%; Observed: C, 38.0% H, 5.9% N, 14.7%.

EXAMPLE 4

Tris-sodium propionyl hexahydrotriazine 40 g of NaOH and 89 g of β-aminopropionic acid are dissolved in 100 ml of water, 30 g of paraformaldehyde are added and the water is subsequently removed azeotropically, followed by filtration under suction and drying.

Analysis for $Na_3C_{12}H_{18}N_3O_6$: Calculated C, 39.4% H, 4.9% N, 11.0%; Observed: C, 39.8% H, 5.7% N, 10.5%.

EXAMPLE 5

Tris-potassium propionyl hexahydrotriazine 56 g of KOH and 89 g of β-aminopropionic acid are dissolved in 100 ml of water, 30 g of paraformaldehyde are added and the water subsequently removed azeotropically, followed by filtration under suction and drying.

Analysis for $K_3C_{12}H_{18}N_3O_6$: Calculated: C, 34.6% H, 4.3% N, 10.1%; Observed: C, 35.8% H, 5.5% N, 9.3%.

EXAMPLE 6

Tris-potassium butyryl hexahydrotriazine 56 g of KOH, 103 g of γ-aminobutyric acid and 30 g of paraformaldehyde are dissolved in 100 ml of water. The water is then removed with toluene, followed by filtration under suction and drying.

Analysis for $K_3C_{15}H_{24}N_3O_6$: Calculated: C, 39.2% H, 5.2% N, 9.2%; Observed: C, 42.8% H, 6.4% N, 10.0%.

EXAMPLE 7

Tris-potassium capropyl hexahydrotriazine 56 g of KOH, 131 g of ε-aminocaproic acid and 30 g of paraformaldehyde are dissolved in 100 ml of water. The water of reaction is then removed with toluene, followed by filtration under suction and drying.

Analysis for $K_3C_{11}H_{21}N_3O_6$: Calculated: C, 48.0% H, 4.0% N, 8.0%; Observed: C, 47.1% H, 5.5% N, 7.2%.

EXAMPLE 8

A polyol mixture is produced from 17 parts, by weight, of a sugar polyether (hydroxyl number 450, starter mixture sugar/water, water content 15 to 35% propylene oxide), 4 parts, by weight, of an aminopolyether (hdroxyl number 650) produced from ethylene diamine and propylene oxide, 10 parts, by weight, of a polyester (functionality 3, hydroxyl number 200) of adipic acid, phthalic acid and diethylene glycol, 1 part, by weight, of a conventional silicone stabilizer and 14 parts, by weight, of trichloroethyl phosphate.

The foaming results obtained using various catalysts are summarized in Table 1.

Batches of 40 parts, by weight, of the abovementioned mixture were intensively stirred for 20 seconds with 20 parts, by weight, of trichlorofluoromethane, the quantity of catalyst indicated in Table 1 and 100 parts, by weight, of a prepolymer of 95 parts, by weight, of crude 4,4'-diphenylmethane diisocyanate, produced by condensing aniline with formaldehyde, followed by phosgenation, NCO-content 31%, by weight, and 5 parts, by weight, of tetrapropylene glycol.

TABLE 1

| Catalyst of Example | 1 | 2 | 4 | 3 | 25% potassium acetate solution in diethylene glycol |
|---|---|---|---|---|---|
| Quantity (pbw) | .3 | 1 | 1.7 | 1.8 | 0.7 |
| Cream time | 155 | 200 | 110 | 120 | 130 |
| Gel Time | 300 | 600 | 300 | 300 | 300 |
| Shrinkage | No | No | No | No | Yes |

The tests show that, with long reaction times, the catalysts of the present invention are advantageous over the potassium acetate normally used because foams activated with them do not shrink. The catalysts of the present invention are preferably used in the form of 20% solutions in diethylene glycol.

EXAMPLE 9

The procedure was as in Example 8. 2 Parts, by weight, of the catalyst solution according to Example 2 (20% in diethylene glycol) are combined with the polyurethane catalysts mentioned in Table 2.

TABLE 2

| Catalysts | A | B | C | D | E |
|---|---|---|---|---|---|
| Quantity | 0.2 | 0.1 | 1 | 0.2 | 0.2 |
| Cream Time | 40 | 60 | 35 | 60 | 23 |
| Gel time | 120 | 160 | 140 | 160 | 90 |

A = dimethyl cyclohexylamine
B = tris-(dimethylaminopropyl)-hexahydrotriazine
C = 2,4,6-tris-(dimethylaminomethyl)-phenol
D = triethyl amine
E = dimethylethanolamine/dibutyl tin dilaurate (ratio by weight 3:1)

None of the foams showed any signs of shrinkage. By contrast, there were signs of shrinkage where a 25% potassium acetate solution was used in conjunction with co-catalysts A to E.

What is claimed is:

1. In a process for the production of polyisocyanurate plastics comprising reacting a polyisocyanate and an isocyanate-reactive compound in the presence of catalyst, the improvement wherein the catalyst is a hexahydrotriazine carboxylate of the formula:

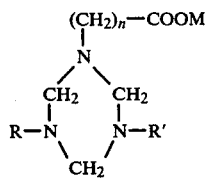

wherein
R and R' which may be the same or different, each represents

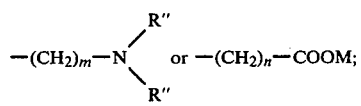

R" represents $C_1$–$C_3$ alkyl;
m represents an integer of from 2 to 6;
n represents an integer of from 1 to 10; and
M represents an alkali metal or $N'''_4$
wherein $NR'''_4$ represents H or $C_1$–$C_4$ alkyl.

2. The process of claim 1, wherein said hexahydrotriazine carboxylate is present in a quantity of from 0.01 to 20%, by weight, based on the polyisocyanate present in the form of a solution of higher alcohols.

3. The process of claim 2, wherein said hexahydrotriazine carboxylate is present in a quantity of 0.1 to 10%.

4. The process of claim 2, wherein said higher alcohol is selected from the group consisting of ethylene glycol, diethylene glycol, dipropylene glycol, and tripropylene glycol.

5. The process of claim 1, wherein said catalyst is selected from the group consisting of tris-sodium acetyl hexahydrotriazine, tris-potassium acetyl hexahydrotriazine, bis-sodium acetyl-α-dimethylaminopropyl hexahydrotriazine, tris-sodium propionyl hexahydrotriazine, and tris-potassium propionyl hexahydrotriazine.

* * * * *